United States Patent [19]
Büschken

[11] Patent Number: 4,788,342
[45] Date of Patent: Nov. 29, 1988

[54] PROCESS FOR PREPARATION OF 4,4,8,8,10-PENTAMETHYLBICYCLO[4,4,0]-DECENE-(1,6)-ONE(2)

[75] Inventor: Wilfried Büschken, Haltern, Fed. Rep. of Germany

[73] Assignee: Hüls Aktiengesellschaft, Marl, Fed. Rep. of Germany

[21] Appl. No.: 85,353

[22] Filed: Aug. 14, 1987

[30] Foreign Application Priority Data

Nov. 22, 1986 [DE] Fed. Rep. of Germany ....... 3639921

[51] Int. Cl.$^4$ .............................................. C07C 45/62
[52] U.S. Cl. ..................................... 568/350; 568/353
[58] Field of Search ................................. 568/350, 353

[56] References Cited

U.S. PATENT DOCUMENTS

| | | | |
|---|---|---|---|
| 3,337,423 | 8/1967 | Schmitt et al. ...................... | 568/353 |
| 3,337,632 | 8/1967 | Schmitt et al. ...................... | 568/350 |
| 3,337,633 | 8/1967 | Schmitt et al. ...................... | 568/350 |
| 4,165,339 | 8/1979 | Reichle ................................ | 568/350 |
| 4,535,187 | 8/1985 | Papa et al. .......................... | 568/353 |

*Primary Examiner*—James H. Reamer
*Attorney, Agent, or Firm*—Gilbert L. Wells

[57] ABSTRACT

4,4,8,8,10-pentamethylbicyclo[4,4,0]-decene-(1,6)-one(2), is produced from the bottom product of the acetone condensation reaction collecting in the production of isophorone by fractionation. A ketone blend consisting essentially of $C_{15}$ compounds where the main components are isomers [B] and [C] as shown in the general formulas:

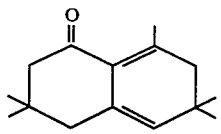

[B]

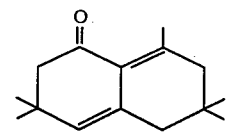

[C]

is isolated. This ketone blend is selectively hydrated in the presence of a noble metal catalyst at hydrogen pressures of 20 to 250 mbars and at temperatures between 25° and 150° C. The 4,4,8,8,10-pentamethylbicyclo[4,4,0]-decene-(1,6)-one(2) is obtained by rectifying the hydration output.

21 Claims, No Drawings

PROCESS FOR PREPARATION OF 4,4,8,8,10-PENTAMETHYLBICYCLO[4,4,0]-DECENE-(1,6)-ONE(2)

CROSS-REFERENCE TO RELATED APPLICATION

Applicant claims priority under 35 USC 119 for application P No. 36 39 921.3 filed Nov. 22, 1986 in West Germany.

BACKGROUND OF THE INVENTION

The field of the invention is the production of isophorone and the invention is particularly concerned with a method for preparing 4,4,8,8,10-pentamethylbicyclo[4,4,0]-decene-(1,6)-one(2) having the general formula:

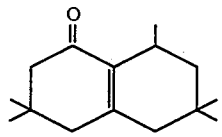

[A]

A $C_{15}$-ketone mixture, such as is obtained by fractionating the bottom product collecting in the production of isophorone, is selectively hydrated at 1 to 100 mbars at an approximate yield of 30%.

The state of the art of isophorone production may be ascertained by reference to the Kirk-Othmer, Encyclopedia of Chemical Technology, 3rd Edition, Vol. 13 (1982), pages 918–922, particularly page 920 and U.S. Pat. Nos. 3,337,423 and 3,337,633, the disclosures of which are incorporated herein by reference.

U.S. Pat. No. 3,337,423 discloses a process for recovering isophorone in high yields from the organic reaction mixture obtained from the condensation of acetone to isophorone wherein said organic reaction mixture includes in addition to isophorone substantially both products having a lower boiling point than isophorone, which comprises passing such organic reaction mixture to a distillation zone having a head, distilling acetone in such distillation zone from an intermixture of such organic reaction mixture with a dilute aqueous alkali solution in a weight ratio of water to organic reaction mixture of from about 0.1 to 10:1 maintained at an elevated temperature, said aqueous alkali solution having an alkali concentration between about 0.001 and 0.1% by weight based on the water present in the aqueous alkali solution, continuously removing from the head of said zone the acetone being distilled, and continuously separately condensing the removed acetone, and recovering isophorone from the intermixture remaining.

U.S. Pat. No. 3,337,633 discloses a process for the production of isophorone from acetone in the presence of alkali, which comprises introducing acetone into a pressure distillation reaction zone, having a head and a sump, at a point intermediate the head solution having a concentration of alkali within the range between 0.02 and 0.1% by weight based on the total liquid content present into said zone at a point intermediate the head thereof and the point at which said acetone is introduced thereinto, distilling said acetone at a temperature of about 100°–250° C. under elevated pressure in said zone in countercurrent contact with said alkali solution between the points of introduction to form in said zone acetone condensation reaction products including isophorone, condensing to liquid form in the head of said zone the acetone being distilled, recovering from said head the condensed liquid acetone and returning a portion thereof to the head as reflux and recycling the remainder of the condensed liquid acetone and returning a portion thereof to the head as reflux and recyling the remainder of the condensed liquid acetone to said zone at said point of introduction of acetone, collecting the alkali solution and said acetone condensation reaction products including isophorone in the sump of said zone, recycling a portion of the collected alkali solution to said zone at said point of introduction of alkali solution, and recovering the condensation reaction products including isophorone from the sump of said zone.

Compound [A] is an appropriate preliminary stage in the synthesis of amines, diamines, heterocycles and a number of other substances. Furthermore it is useful as a scent. When isophorone is made by acetone-condensation, up to 10% of condensation products of higher molecular weights are produced, which presently are burnt off. There was a need therefore to separate this mixture or to react it into valuable products.

SUMMARY OF THE INVENTION

Having in mind the limitations of the prior art, it is an object of the present invention to find a use for the 10% of condensation products of higher molecular weights produced in the sump of the acetone condensation production of isophorone.

The object is achieved by a process for preparing 4,4,8,8,10-pentamethylbicyclo[4,4,0]-decene-(1,6)-one(2) wherein the bottom product collected in the production of isophorone according to U.S. Pat. Nos. 3,337,423 and 3,337,633 is fractionated at pressures between 1 and 100 mbars and a ketone blend is obtained consisting essentially of $C_{15}$ compounds of which the main components are isomers [B] and [C] having the general formulas:

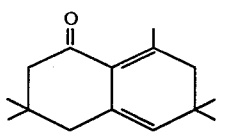 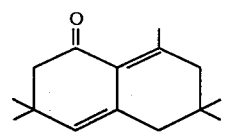

[B]　　　　　　　[C]

The isomers are isolated and selectively hydrated in the presence of a noble metal catalyst at hydrogen pressures of 20 to 250 bars and at temperatures between 25° to 150° C. and the hydrated output is rectified to separate 4,4,8,8,10-pentamethylbicyclo[4,4,0]-decene-(1,6)-one(2).

DESCRIPTION OF THE PREFERRED EMBODIMENTS

Surprisingly it is found that it is easy to commercially obtain compound [A] in good yields by means of industrial process steps by selectively hydrating a special fraction of the bottom product of the isophorone.

When the isophorone bottom product is fractionated at 1 to 100 and preferably at 10 to 30 mbars, a ketone blend is obtained which consists essentially of $C_{15}$ compounds. This ketone blend is obtained at a yield of about 30% and boils at 125° to 145° C. at 13 mbars. The main components of this blend are the isomers [B] and [C] as indicated by the general formulas:

[B]     [C]

The position of the double bonds of compounds [B] and [C] is not entirely assured.

The ratio of the two isomers [B] and [C] is not constant. Again the content of the two materials may vary in the $C_{15}$ fraction. The sum of the isomers is 70 to 90% by weight referred to the $C_{15}$ fraction.

The hydration of the $C_{15}$ ketone blend as a rule results in a very complex reaction mixture. When nickel catalysts are used, the corresponding saturated alcohols (up to 16 isomers) are obtained from the compounds [B] and [C]. When compounds [B] and [C] are hydrated at a palladium catalyst, and higher temperatures and pressures, saturated ketones (up to 8 isomers) are obtained.

Surprisingly it is found that it is possible to selectively hydrate both compounds [B] and [C] almost in quantitative yields into the same ketone [A] provided that the hydration is carried out at low temperatures between 25° and 150° C. and at hydrogen pressures of 20 to 250 bars using a noble metal catalyst.

Preferably the hydration is carried out at temperatures between 80° and 100° C. Preferably the hydration is carried out at hydrogen pressures of 80 to 150 bars. Noble-metal contacts are suitable as the hydration catalysts, for instance catalysts in the platinum group, for instance palladium, platinum. Commercial contact catalysts are useful, illustratively Pd/C or $Pd/Al_2O_3$. As a rule these support catalysts have noble-metal contents of 0.1 to 2, preferably 0.5 to 2% by weight. Palladium support catalysts are preferred.

Slight super-hydrations of compound [A] can be avoided by adding alcohols, in particular methanol. The alcohol is added preferably in amounts of 10 to 60% relative to the hydration substance.

Hydration can be continuous or intermittent. Some of the byproducts are hydrated into materials with another boiling apparatus than used for ketone [A] whereby the major part of the accompanying materials, are separated by rectification.

When the hydration conditions are observed, selective hydration provides stable products. Therefore the hydration time is not critical. After-hydration does not further hydrate the 4,4,8,8,10-pentamethylbicyclo[4,4,0]-decene-(1,6)-one(2), as shown by Examples 7 and 8.

EXAMPLES

EXAMPLE 1

By condensing the acetone, the bottom product of isophorone synthesis disclosed in Example 1 of U.S. Pat. No. 3,337,423 is fractionated at a pressure of 13 mbars. At a yield of about 30%, a ketone blend ($K_{p3}$: 125° to 145° C. is obtained, which essentially consists of $C_{15}$ compounds having main components [B] and [C].

A solution of 300 g of this $C_{15}$ ketone blend (64% by weight [B], 12.6% by weight [C]) and 700 ml of methanol is hydrated in a 2-liter autoclave on a 50 g support catalyst of 2% Pd/C for 3 hours at 80° C. and at a pressure of 100 bars. After the catalyst is filtered off and the methanol is removed, a solution containing 76.6% of [A], 0% of [B] and 0% of [C] is obtained. The pure compound [A] is obtained by rectification.

EXAMPLE 2

1,000 g of $C_{15}$ ketone blend (65% [B], 13.3% [C]) obtained according to Example 1 are hydrated in a 2-liter autoclave on 50 g of a 2% Pd/C support catalyst for 3 hours at 80° C. and a pressure of 100 bars. Following filtering off the catalyst, a solution is obtained containing 77.8% of [A], 0% of [B] and 0% of [C].

EXAMPLE 3

100 ml of a $C_{15}$ ketone blend (58.9% [B], 16.5% [C]) prepared according to Example 1 are hydrated in a 200 ml autoclave on 5 g of a 2% Pd/C support catalyst for 5 hours at 80° C. and a pressure of 145 bars. After the catalyst is removed, a filtrate containing 70% [A], 0% [B] and 0% [C] is obtained.

EXAMPLE 4

A solution of 70 ml of a $C_{15}$ ketone blend (58.9% [B]; 16% [C]) and 30 ml of methanol is hydrated in a 200 ml autoclave on a 5 g support catalyst of 2% Pd/C for 5 hours at 80° C. and a pressure of 145 bars. After the catalyst and the methanol are removed, a solution with 73.5% [A], 0% [B] and 0% [C] is obtained.

EXAMPLE 5

100 ml of a $C_{15}$ ketone blend (58.9% [B]; 16.5% [C]) is hydrated in a 200 ml autoclave on 5 g of a support catalyst of 0.5% $Pd/A_2O_3$ for 5 hours at 80° C. and a pressure of 145 bars. After the catalyst is filtered off, a filtrate containing 69.3% [A], 0% [B] and 0% [C] was obtained.

EXAMPLE 6

A solution of 70 ml of a $C_{15}$ ketone blend (58.9% [B], 16.5% [C]) and 30 ml of methanol is hydrated in a 200 ml autoclave on 5 g of 0.5 $Pd/Al_2O_3$ support catalyst for 5 hours at 80° C. and a pressure of 145 bars. After the catalyst and the methanol are removed, a solution containing 74.3% of [A], 0% of [B] and 0% of [C] is obtained.

EXAMPLE 7 (after-hydration)

100 ml containing 89.2% [A] is hydrated in a 200 ml autoclave on a 5 g support catalyst of 0.5% $Pd/Al_2O_3$ for 5 hours at 80° C. and a pressure of 145 bars. After the catalyst is removed, a solution containing 82.7% [A] is obtained.

EXAMPLE 8 (after-hydration)

A solution of 70 ml of 89.2% [A] and of 30 ml of methanol is hydrated in a 200 ml autoclave on a 5 g support catalyst containing 0.5% $Pd/Al_2O_3$ for 5 hours at 80° C. and a pressure of 145 bars. After the catalyst was separated, and the methanol removed, a solution containing 89.1% [A] is obtained.

I claim:

1. A process for preparing 4,4,8,8,10-pentamethylbicyclo [4,4,0]-decene-(1,6)-one(2), comprising:
   (a) carrying out a condensation reaction of acetone to isophorone in a pressure distillation reaction column having a bottom product wherein a pressure of about 30 atmospheres gage is maintained in said column having a head temperature of about 205 degrees Centigrade and a sump temperature of about 235 degrees Centigrade;

(b) fractionalizing said bottom product at pressures between 1 and 100 mbars and a head temperature of about 125 to 145 degrees centigrade and isolating ketone blend consisting essentially of C₁₅ compounds comprising predominantly isomers [B] and [C] having the following general formulas:

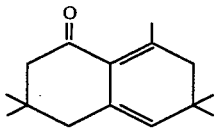 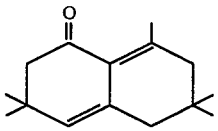

[B]  [C]

(c) selectively hydrating said isolated ketone blend in the presence of a noble metal catalyst selected from the group consisting of platinum and palladium at hydrogen pressures of 20 to 250 bars and at temperatures between 25° and 150° C. to produce a hydrated output; and (d) separating said 4,4,8,8,10-pentamethylbicyclo [4,4,0]-decene-(1,6)-one(2) from said hydrated output.

2. A process for preparing 4,4,8,8,10-pentamethylbicyclo [4,4,0]-decene-(1,6)-one(2), from a ketone blend consisting essentially of C₁₅ compounds comprising predominantly isomers [B] and [C] having the following general formulas:

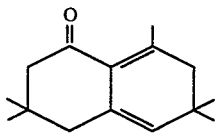 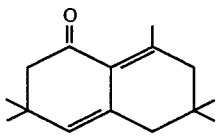

[B]  [C]

comprising:

(a) selectively hydrating said ketone blend in the presence of a noble metal catalyst selected from the group consisting of platinum and palladium at hydrogen pressures of 20 to 250 bars and at temperatures between 25° and 150° C. to produce a hydrated output; and (b) separating said 4,4,8,8,10-pentamethylbicyclo [4,4,0]-decene-(1,6)-one(2) from said hydrated output.

3. The process of claim 1, wherein step (b) is carried out at a pressure of about 13 mbars.

4. The process of claim 1, wherein said noble metal catalyst is palladium.

5. The process of claim 1, wherein said hydration step is carried out at hydrogen pressures of 80 to 150 bars.

6. The process of claim 1, wherein said hydration step (c) is carried out at temperatures between 80° to 100° C.

7. The process of claim 1, wherein said hydration step is carried out following addition of an alcohol.

8. The process of claim 7, wherein said alcohol is methanol.

9. The process of claim 1, wherein said isomers are 70 to 90% by weight of said C₁₅ compounds.

10. The process of claim 4, wherein said palladium is supported on carbon.

11. The process of claim 4 wherein said palladium is supported on Al₂O₃.

12. The process of claim 4, wherein said catalyst is a support catalyst having a palladium content of 0.1 to 2% by weight.

13. The process of claim 2, wherein said noble metal catalyst is palladium.

14. The process of claim 2, wherein said hydration step [a] is carried out at hydrogen pressures of 80 to 150 bars.

15. The process of claim 2, wherein said hydration step [a] is carried out at a temperature between 80° and 100° C.

16. The process of claim 2, wherein said hydration step [a] is carried out following addition of an alcohol.

17. The process of claim 16, wherein said alcohol is methanol.

18. The process of claim 2, wherein said isomers are 70 to 90% by weight of said C₁₅ compounds.

19. The process of claim 13, wherein said palladium is supported on carbon.

20. The process of claim 13, wherein said palladium is supported on Al₂O₃.

21. The process of claim 13, wherein said catalyst is a support catalyst having a palladium content of 0.1 to 2% by weight.

* * * * *